(12) United States Patent
Ashtarolnakhai et al.

(10) Patent No.: US 11,590,320 B2
(45) Date of Patent: Feb. 28, 2023

(54) TWO-IN-ONE CATHETER AND SIGNAL GENERATING APPARATUS

(71) Applicant: Avent, Inc., Alpharetta, GA (US)

(72) Inventors: Shadi Ashtarolnakhai, Sandy Springs, GA (US); Veerdhaval V. Mahajan, Cumming, GA (US); Kelley R. Biehl, Roswell, GA (US); Audra Wright, Woodstock, GA (US)

(73) Assignee: Avent, Inc., Alpharetta, GA (US)

( * ) Notice: Subject to any disclaimer, the term of this patent is extended or adjusted under 35 U.S.C. 154(b) by 99 days.

(21) Appl. No.: 16/375,227

(22) Filed: Apr. 4, 2019

(65) Prior Publication Data

US 2020/0316341 A1   Oct. 8, 2020

(51) Int. Cl.
| | | |
|---|---|---|
| A61M 25/01 | (2006.01) | |
| A61J 15/00 | (2006.01) | |
| A61L 29/12 | (2006.01) | |
| A61L 29/14 | (2006.01) | |
| A61M 25/00 | (2006.01) | |

(52) U.S. Cl.
CPC ...... *A61M 25/0127* (2013.01); *A61J 15/0088* (2015.05); *A61L 29/126* (2013.01); *A61L 29/14* (2013.01); *A61M 25/0045* (2013.01); *A61M 2205/0283* (2013.01)

(58) Field of Classification Search
CPC ................ A61J 15/0088; A61J 15/0003; A61J 15/0084; A61M 25/0045; A61M 2205/0283

See application file for complete search history.

(56) References Cited

U.S. PATENT DOCUMENTS

| | | | |
|---|---|---|---|
| 4,836,214 A | 6/1989 | Sramek | |
| 4,921,481 A | 5/1990 | Danis et al. | |
| 6,334,064 B1 | 12/2001 | Fiddian-Green | |
| 6,357,447 B1 | 3/2002 | Swanson et al. | |
| 7,818,155 B2 | 10/2010 | Stuebe et al. | |
| 7,976,518 B2 | 7/2011 | Shaughnessy et al. | |
| 8,147,486 B2 | 4/2012 | Honour et al. | |
| 8,197,494 B2 | 6/2012 | Jaggi et al. | |
| 8,265,732 B2 | 9/2012 | Besz et al. | |
| 8,606,347 B2 | 12/2013 | Besz et al. | |
| 8,613,702 B2 | 12/2013 | Feer et al. | |
| 8,934,960 B2 | 1/2015 | Besz et al. | |
| 8,986,230 B2 | 3/2015 | Nishtala | |
| 9,131,956 B2 | 9/2015 | Shaughnessy et al. | |

(Continued)

FOREIGN PATENT DOCUMENTS

WO        WO 92/17150        10/1992

OTHER PUBLICATIONS

International Search Report and Written Opinion for PCT/US2020/026298, dated Jul. 15, 2020, 14 pages.

*Primary Examiner* — Lauren P Farrar
(74) *Attorney, Agent, or Firm* — Dority & Manning, P.A.

(57) ABSTRACT

A tubing assembly includes a signal generating apparatus for a catheter placement system. The tubing assembly includes a catheter and a signal generating apparatus. The catheter includes an elongate shaft having a wall surrounding a lumen. The signal generating apparatus includes at least one electromagnetic coil and at least one electrically conductive polymer that is configured to electrically connect the at least one electromagnetic coil to a monitor unit.

20 Claims, 4 Drawing Sheets

(56) References Cited

U.S. PATENT DOCUMENTS

| | | |
|---|---|---|
| 9,179,971 B2 | 11/2015 | Kirschenman |
| 9,226,878 B2 | 1/2016 | Elia et al. |
| 9,295,395 B2 | 3/2016 | Elia et al. |
| 9,532,739 B2 | 1/2017 | Bennett-Guerrero |
| 9,579,488 B2 | 2/2017 | Shaughnessy et al. |
| 9,585,599 B2 | 3/2017 | Besz et al. |
| 9,610,227 B2 | 4/2017 | Elia |
| 9,642,779 B2 | 5/2017 | Elia et al. |
| 9,687,174 B2 | 6/2017 | Jaggi et al. |
| 9,713,579 B2 | 7/2017 | Elia et al. |
| 9,889,277 B2 | 2/2018 | Shaughnessy et al. |
| 10,058,268 B2 | 8/2018 | Besz et al. |
| 2005/0165301 A1* | 7/2005 | Smith ............... A61M 25/0127 600/421 |
| 2006/0241734 A1 | 10/2006 | Marshall et al. |
| 2008/0097179 A1 | 4/2008 | Russo |
| 2008/0167607 A1 | 7/2008 | Pfeiffer et al. |
| 2008/0249467 A1 | 10/2008 | Burnett et al. |
| 2009/0171349 A1* | 7/2009 | Byrd ................... A61B 18/1492 606/41 |
| 2010/0036229 A1* | 2/2010 | Weekamp ........... A61J 15/0084 600/380 |
| 2010/0179417 A1* | 7/2010 | Russo ................... A61M 39/08 600/424 |
| 2012/0016256 A1 | 1/2012 | Mabary et al. |
| 2012/0226148 A1 | 9/2012 | Jaggi et al. |
| 2012/0277619 A1 | 11/2012 | Starkebaum et al. |
| 2012/0323089 A1* | 12/2012 | Feer ..................... A61B 5/0538 600/301 |
| 2013/0225946 A1 | 8/2013 | Feer et al. |
| 2016/0113843 A1 | 4/2016 | Elia et al. |
| 2016/0129223 A1 | 5/2016 | Kirschenman |
| 2016/0331298 A1 | 11/2016 | Burnett et al. |
| 2016/0354160 A1* | 12/2016 | Crowley ................ A61B 10/04 |
| 2017/0071502 A1 | 3/2017 | Bennett-Guerrero |
| 2017/0202750 A1 | 7/2017 | Elia |
| 2018/0078195 A1 | 3/2018 | Sutaria et al. |
| 2018/0161249 A1 | 6/2018 | Elia et al. |
| 2018/0289536 A1 | 10/2018 | Burnett |

* cited by examiner

TWO-IN-ONE CATHETER AND SIGNAL GENERATING APPARATUS

FIELD OF THE INVENTION

The subject matter of the present invention relates generally to a tubing assembly having a catheter and a signal generating apparatus integrated therein.

BACKGROUND

Physicians and other health care providers frequently use catheters to treat patients. The known catheters include a tube which is inserted into the human body. Certain catheters are inserted through the patient's nose or mouth for treating the gastrointestinal tract. These catheters, sometimes known as enteral catheters, typically include feeding tubes. The feeding tube lies in the stomach or intestines, and a feeding bag or pump delivers liquid nutrient, liquid medicine or a combination of the two to the patient.

Other types of catheters are inserted into the patient's veins or arteries for treating the cardiovascular system. These intravascular catheters include, among others, the central venous catheter, peripheral venous catheter and the peripherally inserted central catheter. These catheters include a relatively small tube that passes through the patient's veins or arteries. Depending on the application, the health care providers can use these intravascular catheters to remove blood vessel blockages, place inserts into blood vessels and to provide patients with injections of medications, drugs, fluids, nutrients, or blood products over a period of time, sometimes several weeks or more.

When using these known enteral and intravascular catheters, it is important to place the end of the catheter at the proper placement within the human body. Erroneous placement of the catheter tip may injure or harm the patient. For example, if the health care provider erroneously places an enteral catheter into the patient's lungs, liquid may be introduced into the lungs with harmful results.

If the health care provider erroneously places an intravascular catheter into the wrong blood vessel of the cardiovascular system, the patient may experience infection, injury, or a harmful blockage.

It is also prudent to check that the exit aperture of the feeding tube (typically located at the distal end/tip of the tube) remains in its desired location over the period of treatment, e.g., feeding. Protocols that address this requirement in enteral feeding tubes include frequent monitoring for the appropriate pH of fluids extracted from the feeding tube when not carrying nutritional liquids and careful patient monitoring to ensure nutritional uptake is as expected.

One existing catheter means to locate a catheter involves using an electromagnetic coil positioned inside the catheter and an electromagnetic coil locating receiver outside of the patient's body to approximate and display the catheter position. However, these systems also have several disadvantages. For example, the electromagnetic coil is included as part of a wire assembly that must be inserted coaxially within the catheter, such as a stylet or a guide wire, and is separate from the catheter itself. Thus, the wire assembly must be re-inserted into the catheter each time the placement of the catheter is checked. Additionally, insertion of the wire assembly into the catheter may risk rupturing the catheter tube, which can then cause physiological damage to the internal organs of the patient.

Consequently, there is a need for a system for locating a catheter that only includes a single component being inserted into the patient. In particular, a catheter having an electromagnetic coil and a conductive polymer embedded therein would also be useful.

SUMMARY

The present invention is directed to a tubing assembly. The tubing assembly includes a catheter having an elongate shaft having an outer wall surrounding a lumen, the elongate shaft having a proximal end and a distal end and extending in a longitudinal direction, wherein the lumen extends from the proximal end to the distal end. The tubing assembly further includes a signal generating apparatus including at least one signal generator and at least one electrically conductive polymer configured to electrically connect the at least one signal generator to a monitor unit.

In one particular embodiment, the signal generating apparatus can be disposed between an inner wall of the elongate shaft and an external surface of the outer wall of the elongate shaft.

In another embodiment, the at least one signal generator of the signal generating apparatus can be encapsulated by the outer wall of the elongate shaft.

In an additional embodiment, the at least one electromagnetic coil can be at the distal end of the elongate shaft.

In a further embodiment, the at least one signal generator can include a plurality of signal generators spaced apart along the elongate shaft.

In yet another embodiment, the at least one signal generator can surround the lumen of the elongate shaft. Moreover, the at least one signal generator can be insulated from the lumen.

In still another embodiment, the at least one electrically conductive polymer can form at least a portion of the outer wall of the elongate shaft. Moreover, the outer wall of the elongate shaft can include an inner layer and an outer layer. Further, the inner layer and the outer layer can coaxially surround the lumen. In addition, the inner layer can include the at least one electrically conductive polymer of the signal generating apparatus. Further, the outer wall can include a single layer, wherein the single layer includes the at least one electrically conductive polymer of the signal generating apparatus.

In one more embodiment, an external surface of the outer wall of the elongate shaft is biocompatible.

In an additional embodiment, the signal generating apparatus can further include a connector assembly configured to transmit at least one electrical signal between the at least one signal generator and the monitor unit.

In still another embodiment, the electrically conductive polymer can be configured to transmit a signal to the at least one signal generator.

In a further embodiment, the electrically conductive polymer can include an intrinsically conductive polymer, a conductor-filled polymer or a combination thereof. Moreover, the electrically conductive polymer can include silicone filled with embedded metallic, carbon, graphite or intrinsically conductive polymer particles or powder.

In one more embodiment, the catheter is a feeding tube.

The present invention is further directed to a signal generating apparatus. The signal generating apparatus includes at least one signal generator, and at least one electrically conductive polymer configured to electrically connect the at least one signal generator to a monitor unit. The at least one signal generator and the at least one electrically conductive polymer are configured to be integrated within a catheter.

In one particular embodiment, the signal generating apparatus can further include a connector assembly configured to transmit at least one electrical signal between the at least one signal generator and a monitor unit.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
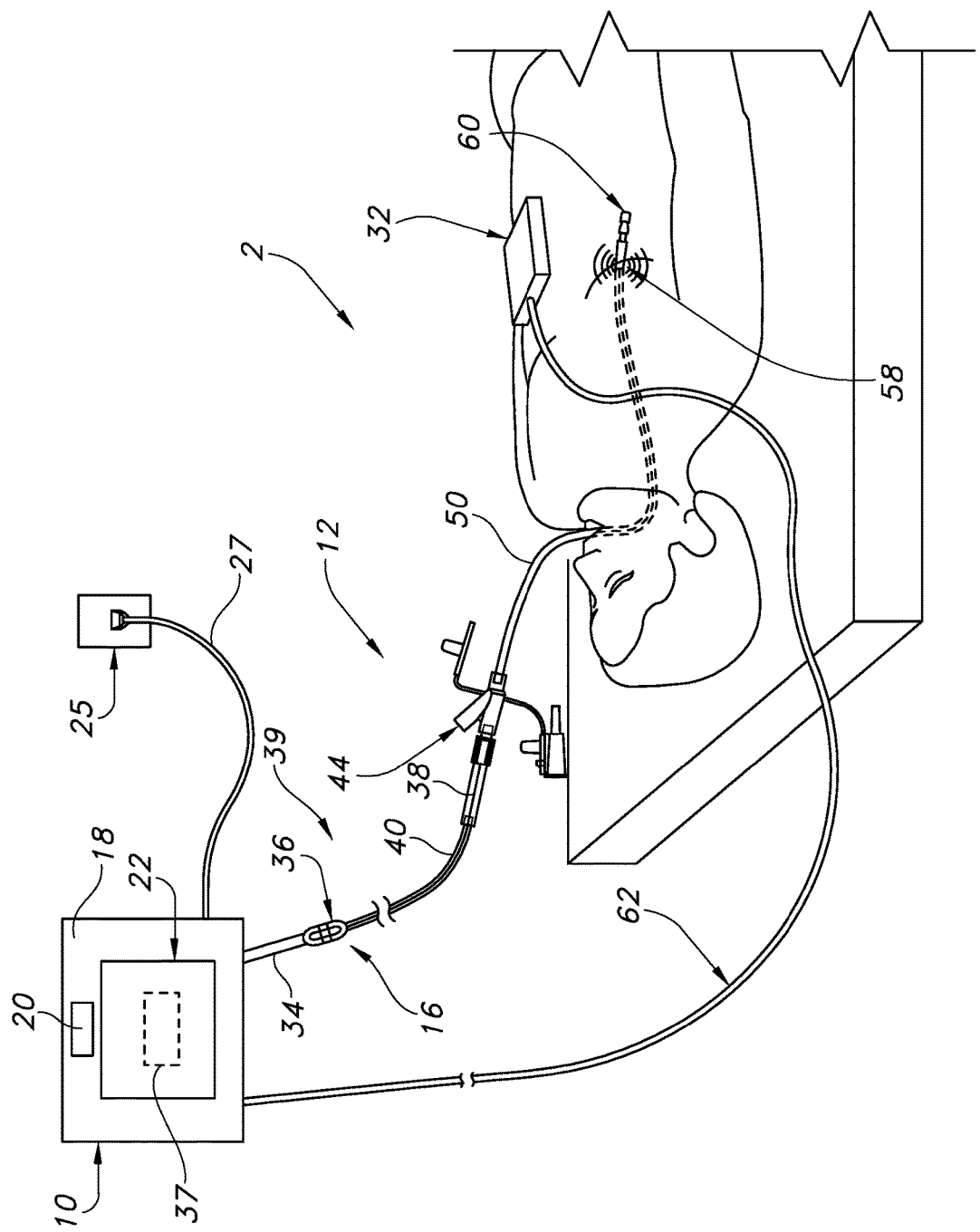
FIG. 1 illustrates a perspective view of a tubing assembly according to one particular embodiment of the present invention in use with a catheter position guidance system.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

Generally speaking, the present invention is directed to a tubing assembly. The tubing assembly includes a catheter. The catheter has an elongate shaft having an outer wall surrounding a lumen, the elongate shaft having a proximal end and a distal end and extending in a longitudinal direction, wherein the lumen extends from the proximal end to the distal end. The tubing assembly further includes a signal generating apparatus including at least one electromagnetic coil and at least one electrically conductive polymer configured to electrically connect the at least one electromagnetic coil to a monitor unit. The present invention is also directed to a signal generating apparatus having a signal generator configured to be encapsulated within a catheter. Because of the specific components of the tubing assembly and the signal generating apparatus, namely, that the signal generator is integrated into the tubing assembly, the present inventors have found that the location and placement of a catheter within a patient's body using a medical device position guidance system can be performed more accurately and with reduced time and effort, and re-confirmation of the placement of the catheter can be more easily achieved. Moreover, the present inventors have found that the specific components of the tubing assembly and signal generating apparatus can result in a safer procedure compared to current solutions which require a signal generator to be inserted within a catheter lumen, which risks rupturing of the catheter tube.

The specific features of the tubing assembly and electronic catheter unit of the present invention may be better understood with reference to FIGS. 1-4B.

Referring now to the drawings, in an embodiment illustrated in FIG. 1, the medical device position guidance system or medical device guidance system 2 includes: (a) a monitor unit 10 having a housing 18 which supports a controller or processor 20 and a display device 22; (b) a non-invasive movable receiver-transmitter or transceiver 32 electronically coupled to the processor 20 by a wire, cable, signal data connection or signal carrier 62; (c) a power cord 27 that couples the monitor unit 10 to a power source 25; and (d) an invasive electronic catheter unit 12 in communication with the transceiver 32 and operatively coupled to the monitor unit 10 by a wire, cable, cord or electrical extension 34, which, in turn, is operatively coupled to the processor 20. In an alternative embodiment, the monitor unit 10 can include an independent power source such as a battery (not shown) in place of the power cord 27 and external power source 25. It should be appreciated that the transceiver 32 can include a device which has a separate signal receiver and signal transmitter. The transceiver 32 can also include a single device which functions so as to receive and transmit signals.

Health care providers can use the system 2 in a variety of catheter applications. In one example illustrated in FIG. 1, the system 2 is used in an enteral application. Here, a portion of the catheter 50 of the electronic catheter unit 12 is placed through the patient's nose or mouth. The distal end or tip 60 of the catheter 50 is positioned in a patient's stomach. The health care provider places the transceiver 32 over the chest area of a patient's body. The display device 22 indicates information related to the location of the portion of the electronic catheter unit 12 within the body, as well as information related to the shape of the pathway taken by the catheter unit 12. It should be appreciated that the system 2 need not indicate the exact location or path of the catheter unit 12 to provide assistance to the health care provider.

As illustrated in FIG. 1, in one embodiment, the electronic catheter unit 12 includes: (a) a tube or an electrical tubular insulator 40; (b) a multi-port connector or y-port connector 44 attachable to the tube 40; (c) a catheter 50, such as a feeding tube, connected to the y-port connector 44; and (d) a catheter end, bolus or tip 60 attached to the distal end of the catheter 50. A signal generating apparatus 16, as will be described in more detail below, can be integrated into the electronic catheter unit 12.

Figure 2:
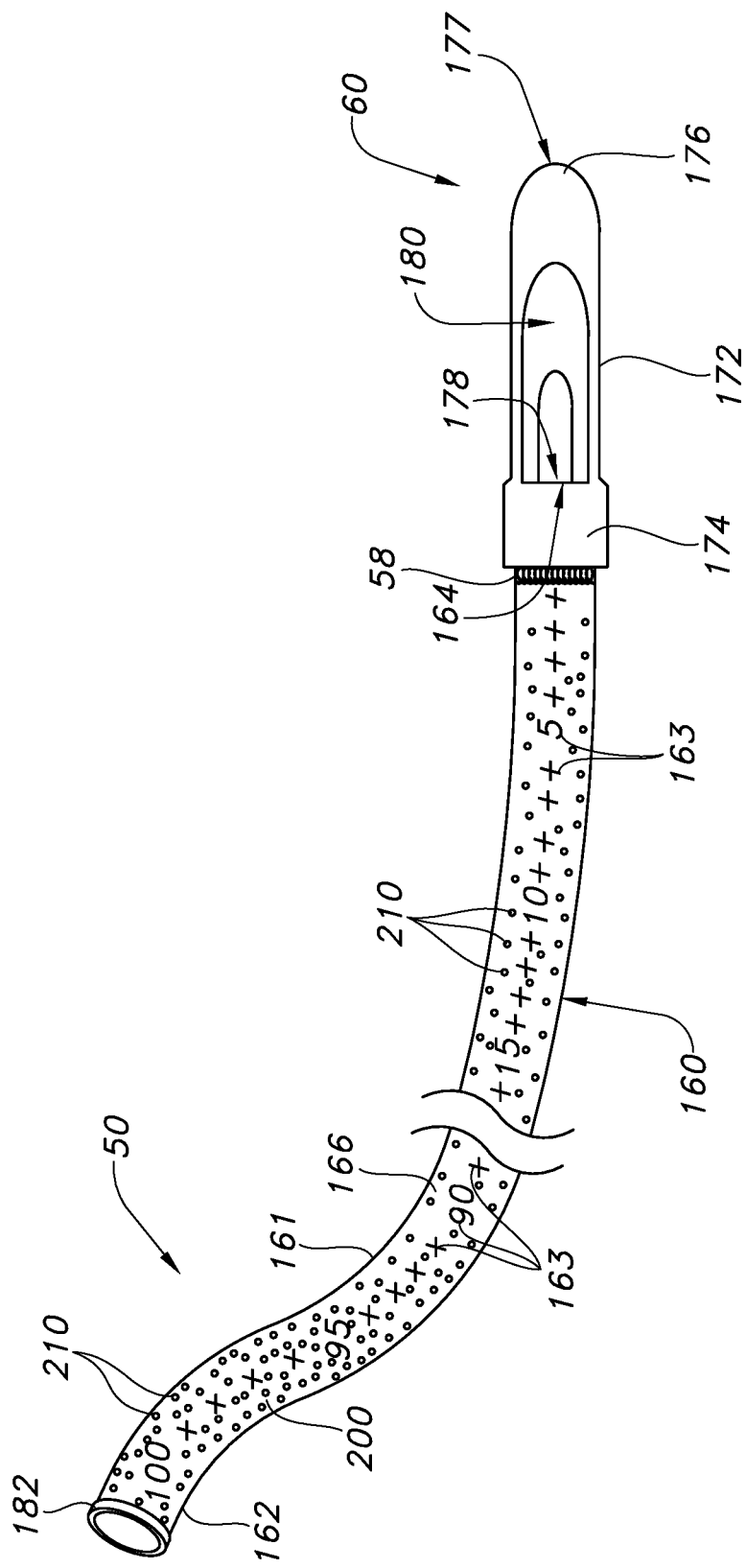
FIG. 2 illustrates a side view of the tubing assembly of FIG. 1.

As illustrated in FIG. 2, in one embodiment, the catheter 50 includes a feeding tube with an elongate shaft 160 having: (a) a proximal end 162 configured to attach to a connector 44 of the signal generating apparatus; (b) a distal end 164; and (c) an outer wall 161 having an external surface 166. The proximal end 162 is insertable into the connector 44 so as to bring the catheter 50 into fluid communication with the y-port connector 44. In one embodiment, the external surface 166 has a plurality of volumetric, measurement or unit markings 163 uniformly spaced along the elongate shaft 160 of the catheter. These markings 163 assist the user in measuring the flow or distribution of liquid to or from the patient. In an alternative embodiment, markings 163 can function as placement markers which assist the user in assessing the depth that the catheter is placed within the human body.

The elongate shaft 160 can be formed from a variety of materials, giving due consideration to the goals of flexibility, lightweight, strength, smoothness, and non-reactivity to anatomical systems, i.e., safety. Suitable materials for the elongate shaft 160 include polyolefins, including polyethylene and polypropylene, polyamides, polyimides, teflon (polytetrafluoroethylene), polyesters, polyurethanes, any copolymers thereof, and other materials known in the art.

Still referring to FIG. 2, in one embodiment, the end member, bolus or tip 60 is attached to the distal end 164 of the catheter 50. The tip 60 includes a body 172 having a collar 174 and an end member 176. The body 172 defines a passage 178 and an opening 180. The opening 180 is positioned between the collar 174 and the end member 176. A portion 177 of the end member 176 can have a rounded shape. The shape of the passage 178 and opening 180 of the tip 60 is configured to facilitate the flow of fluid from the catheter 50 into the patient's body while decreasing the likelihood that the opening 180 will become clogged. The tip 60 can be made from any suitable polymer or plastic material including, but not limited to, polyamide, polyethylene, polypropylene, polyurethane, silicone and polyacrylonitrile.

The catheter 50 can be a feeding tube, as explained above. The catheter 50 can be a catheter tube having a size in a range from 5 gauge to 20 gauge, such as, for example, 6.5 gauge, or 8 gauge, or 10 gauge, or 12 gauge, or 14 gauge, or 16 gauge, or 18 gauge. The catheter 50 can have a length in a range from about 10 inches (25 cm) to about 60 inches (152 cm), or any range or value therebetween, such as from about 12 inches (30 cm) to about 48 inches (122 cm), for example from about 15 inches (38 cm) to about 30 inches (76 cm).

The invasive electronic catheter unit 12 additionally can include a signal generating apparatus 16 including: (a) a controller coupler or an electrical connector 36 operatively connected to the electrical extension 34; (b) an elongated wire or cable assembly 38 operatively coupled to the connector 36; (c) at least one conductive polymer 200 incorporated into the elongate shaft 160 of the catheter 50 and operatively coupled to the elongated wire assembly 38; (d) a signal generator 58, e.g., a magnetic energy generator or magnetic field generator, operatively coupled to the at least one conductive polymer. The tube 40 described above can cover the wire assembly 38 between the connector 44 and the connector 36. In one embodiment, the wire assembly 38 can include an additional wire or elongated stiffener attached to the connector 38 and serving as a support for the wire assembly 38. Together, the wire assembly 38, connector 36, and tube 40 can form a connector assembly 39 configured to operatively, i.e. electrically, connect the conductive polymer 200 to the monitor unit 10, thereby operatively connecting the signal generator 58 to the monitor unit 10.

In one embodiment, as shown in FIGS. 2-3 and 4A-B, the signal generator 58 can be a magnetic field generator that is formed by a plurality of spirals or coils of wires. For example, the signal generator 58 can be formed through a plurality of spirals or coils of conductive copper wire, or any other electrically conductive wire. As illustrated in FIG. 2, in one embodiment, the signal generating apparatus 16 can include a single coil signal generator 58 at or near the distal end 164 of the elongated shaft 160. The single coil signal generator 58 can have a diameter in a range from about 0.01 inches (0.25 mm) to about 0.2 inches (5.1 mm), or any range or value therebetween, such as from about 0.02 inches (0.51 mm) to about 0.15 inches (3.8 mm), for example from 0.03 inches (0.75 mm) to about 0.1 inches (2.5 mm). In another embodiment, illustrated in FIG. 3, the signal generating apparatus can include a plurality of signal generator coils 58 spaced apart at or near the distal end 164 of the elongated shaft 160. In the embodiment having a plurality of signal generator coils 58, the signal generating apparatus 16 has multiple transmitting points along the elongate shaft 160 of the catheter 50.

Figure 4A:
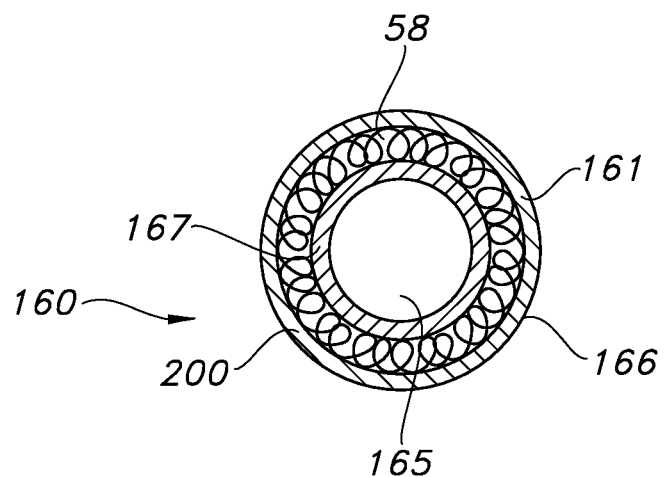
FIGS. 4A-B illustrate cross-sectional views of the catheter according to embodiments of the present invention.
Figure 4B:
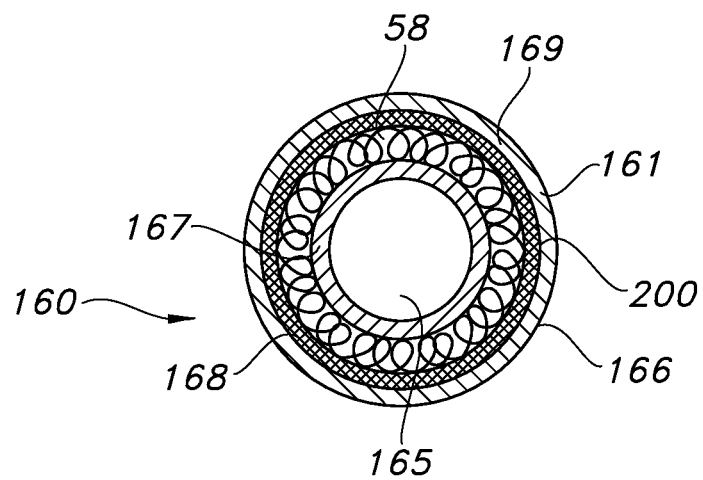

As shown in FIGS. 4A-B, the signal generator 58 can be encapsulated within the outer wall 161 of the elongate shaft 160 of the catheter 50. The encapsulated signal generator 58 can be positioned between the inner wall 167 and the external surface 166 of the outer wall 161 of the elongated shaft 160. For example, the encapsulated signal generator 58 can be surrounded by the outer wall 161, as shown in FIGS. 4A-B or can be integrally formed or embedded within the outer wall 161. In one embodiment, as shown in FIGS. 4A-B, the signal generator 58 can at least partially surround or encircle the lumen 165 of the elongate shaft 160. The lumen 165 can be surrounded by the inner wall 167 disposed between the signal generator 58 and the lumen 165 to prevent the signal generator 58 from being in fluid communication with the lumen 165 or any fluid flowing through the lumen 165.

The elongate shaft 160 having at least one signal generator 58 encapsulated therein can be formed from a variety of manufacturing processes. A non-limiting example of a manufacture process suitable for forming the elongate shaft 160 around the signal generator 58 is the extrusion of the outer wall 161 around the signal generator 58, extrusion of the signal generator 58 within the outer wall 161 or molding of the outer wall 161 around the coil 58.

As illustrated in FIG. 2, the signal generating apparatus 16 can include a conductive polymer 200 configured to operatively, i.e. electrically, connect the signal generator(s) 58 with the elongated wire assembly 38. The conductive polymer 200 can be integrated with the outer wall 161 of the elongate shaft 160 of the catheter 50. For example, the entire outer wall 161 can be formed from a layer of a conductive polymer 200 as long as the conductive polymer 200 on the external surface 166 of the outer wall 161 is biocompatible. FIG. 4A illustrates an embodiment of a catheter 50 having an elongate shaft 160 having an outer wall 161 formed from a conductive polymer 200 that is formed by embedding conductive particles 210 within a non-conductive material, e.g. silicone, of the outer wall 161 or by utilizing an intrinsically conductive polymer to form the outer wall 161. The conductive polymer 200 should be selected with due consideration to the goals of flexibility, lightweight, strength, smoothness, and non-reactivity to anatomical systems, i.e., safety. The conductive polymer 200 will be described in greater detail below.

Figure 3:
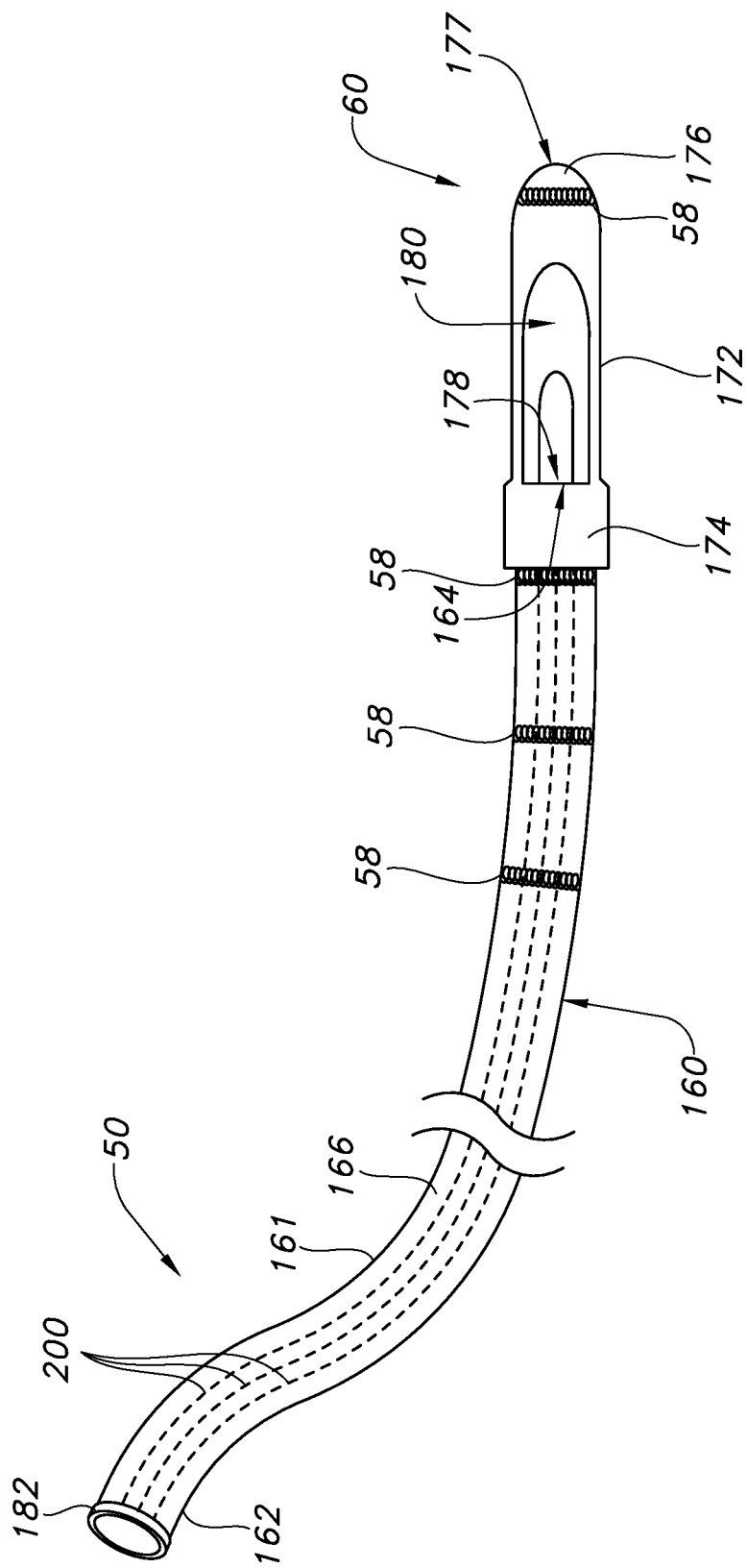
FIG. 3 illustrates a side view of a tubing assembly of another embodiment of the present invention.

In another embodiment, as shown in FIG. 4B, the outer wall 161 can be formed from at least two layers including an inner layer 168 of conductive polymer 200 and an outer layer 169 forming the external surface 166 of the wall 161. In the embodiment of FIG. 4B, the conductive polymer 200 is in electrical communication with the signal generator 58, while the inner wall 167 insulates the lumen 165 from the conductive polymer 200 of the inner layer 168 and the outer layer 169 insulates the external surface 166 from the conductive polymer 200. The inner layer 168 of conductive polymer 200 can be concentric with the outer layer 169 of the outer wall 161, as shown in FIG. 4B. Alternatively, the inner layer 168 of conductive polymer 200 may not be concentric with the outer layer 169 of the outer wall 161. For example, the inner layer 168 can extend around only a portion of the radius of the outer wall 161, such as extending along the length of the elongate shaft 160 within the outer layer 169 of the outer wall 161. In one embodiment, inner layer 168 can be discontinuous around the radius of the outer wall 161, for example forming multiple elongate segments of conductive polymer 200 as shown in FIG. 3. The discontinuous segments of conductive polymer 200 can be generally linear and parallel, as shown in FIG. 3, or can be non-linear and/or non-parallel, such as having intersecting segments of conductive polymer 200 along the length of the elongate portion 160. In other embodiments, the conductive polymer 200 can be arranged in the elongate shaft 160 in any pattern, shape or arrangement suitable for conducting electrical energy from the proximal end 162 of the elongate shaft 160 to a signal generator 58 within the elongate shaft 160.

Any non-conductive portions of the elongate shaft 160, e.g., the inner wall 167 and the outer layer 169 of the outer wall 161, can be formed from a variety of materials, giving due consideration to the goals of flexibility, lightweight, strength, smoothness, and non-reactivity to anatomical systems, i.e., safety. For example, the non-conductive portions of elongate shaft 160, such as the inner wall 167 and the outer layer 169 of the outer wall 161, can include any suitable material that is utilized in medical tubing, such as polytetrafluoroethylene (Teflon), polyethylene, polyurethane, silicone, or a combination thereof.

As used herein, the term "conductive polymer" refers to a polymer that is formed using at least some conductive materials and which is conductive even in its quiescent state. The present invention will work with various conductive polymer materials. For example, intrinsically conductive and conductor-filled polymers may be useful in the present invention. Intrinsically conductive polymers can include polypyrrole, poly(3,4-ethylenedioxythiophene), polythiophene, polyaniline, poly-p-phenylene-sulphide, polyacetylene, polyisoprene, polybutadiene, or a combination thereof. Conductor-filled polymers may include presently available materials approved for implantation such as silicone rubber with embedded conductive particles 210 such as metallic, carbon or graphite particles or powder, or particles of the intrinsically conductive polymers listed above. Silver filled silicone rubbers of the kind manufactured by NuSil Technology LLC or Specialty Silicone Products, Inc. modified so as to be approved for implantation, are of potential utility. An example is silver-coated, nickel-filled silicone rubber sold as NUSIL® R2637. The substrate of a conductor-filled polymer need not be silicone; for example, it is contemplated that other insulating or weakly conductive materials (e.g., non-conductive elastomers) may be embedded with conductive materials, conductive alloys, and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium, and metals of the lanthanide and actinide series, and, if appropriate, at least one electroconductive agent). The conductive material may be in the form of powder, grains, fibers, or other shaped forms. The oxides can be mixtures comprising sintered powders of an oxycompound. The alloy may be conventional, for example titanium boride.

For example, one conductor-filled polymer is silicone filled with carbon black. Carbon black can be made to have good conductivity, good polymeric (flexible and strong) mechanical properties, and good adhesion properties to metal. As such, carbon black can be used as the conductive filler. Carbon black is also quite inert. Therefore, a carbon black filled silicone has been found to be compatible as well as biostable in this application. Also, carbon black filled silicone is solid, which makes it different from other porous conductive materials, e.g., ETFE (ethylene-tetrafluoroethylene) porous tubing. As such, cell in-growth can be prevented.

Preferably, the conductive polymer material will also be biocompatible and meet cytotoxicity, hemolysis, systemic toxicity and intracutaneous injection standards. As shown in FIGS. 1 and 2, at the proximal end 162 of the elongate shaft 160, the conductive polymer 200 can connect to the wire assembly 38. For example, the connector 44 can include at least one electrical contact configured to be in electrical communication with the conductive polymer 200 of the elongate member 160. The wire assembly 38 can extend within the tube 40 to the connector 44 and electrically connect with the connector 44. In an alternative embodiment, the wire assembly 38 can connect directly to the conductive polymer 200 at the proximal end 162 of the elongate shaft 160, such as by a clip, pin, or any other suitable electrical connector. In one embodiment, as shown in FIGS. 2 and 3, proximal end 162 of the elongate shaft 160 can include a conductive metal ring 182 that can be in electrical communication with the conductive polymer 200. The connector 44 can receive the wire assembly 38 therein to establish a protective cover over the electrical connection between the wire assembly 38 and the proximal end 162 of the elongate shaft 160. As explained above, the wire assembly 38 is in electrical communication with the electrical cord 34 of the monitor unit 10, such as via electrical connector 36.

In use, the monitor unit 10 or any other power source can send electrical current to the signal generator(s) 58 through the electrical cord 34, wire assembly 38 and conductive polymer 200. The signal generator(s) 58 transmit a signal or electromagnetic field that is capable of being detected by the non-invasive transceiver 32, as shown in FIG. 1. The transceiver 32 detects the electromagnetic field generated by the signal generator(s) 58 inside the human body. The processor 20 receives signals from the transceiver 32 regarding the relative positioning of the transceiver relative to the signal generator(s) 58 and causes the display device 22 to produce graphics 37 (shown in FIG. 1) which assist the heath care provider in the catheter placement procedure. When the elongate shaft 160 having the conductive polymer 200 is disconnected from the wire assembly 38, the conductive polymer 200 stops transmitting any electrical signals or impulses.

In an alternative embodiment (not shown), the electronic catheter unit 12 can include an independent control unit having a processor, a memory unit, a battery, and a wireless communication means configured to communicate with the monitor unit 10. The processor of the electronic catheter unit 12 can send an electromagnetic drive signal to send an electrical current from the battery to the signal generator(s) 58. The wireless communication means can send information regarding the electromagnetic drive signal to the monitor unit 10, which can then be received by the processor 20. The processor 20 can receive signals from the transceiver 32 regarding the relative positioning of the transceiver relative to the signal generator(s) 58 and can cause the display device 22 to produce graphics 37 which can thereby assist the heath care provider in the catheter placement procedure.

Because of the specific components of the tubing assembly and the signal generating apparatus 58, namely, that the signal generator 58 is integrated into the tubing assembly 50, the present inventors have found that the location and placement of a catheter within a patient's body using the medical device position guidance system 2 can be performed more accurately and with reduced time and effort. Further, re-confirmation of the placement of the catheter can be more easily achieved since no stylet or wire assembly needs to be inserted within the catheter to visualize the placement. Moreover, the present inventors have found that the specific components of the tubing assembly and signal generating apparatus can result in a safer procedure compared to current solutions that require a signal generator to be inserted within a catheter lumen, as inserting a stylet or wire assembly can risk rupturing of the catheter tube. In addition, the present inventors have found that the particular arrangement of the present invention including the conductive polymer 200 in the elongate shaft 160 to transmit signals to the signal generator 58 can enable the medical device guidance system 2 to be used with, or reduce interference with, other imaging such as magnetic resonance imaging (MRI). For example, an MRI of the brain or other anatomical part of the body can be performed while the feeding tube 50 is intubated within a patient because the conductive polymer 200 would not interfere with the MRI in the same way that a wire assembly inserted within the feeding tube would. In a non-limiting example use of the present invention, a catheter 50 of the medical device guidance system 2 could be used to inject MRI contrast into the patient's body for a MRI procedure.

Although the above embodiments related to a medical device guidance system describe a catheter having a conductive polymer and a signal generator embedded therein that can be used for, e.g., a feeding tube, it should be appreciated that the medical device guidance system is operable to assist in the placement of any medical device or invasive component into a mammal in the course of stent placement, ablation, blockage removal, heat treatment, surgical procedure, fluid delivery or any other suitable invasive procedure. It should be appreciated that any type of catheter may be used for any of the medical procedures described above and can include a conductive polymer and signal generator as described. It should also be appreciated that any suitable invasive medical device can include the conductive polymer and signal generator as described and be used in place of a catheter.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A tubing assembly comprising:
    an enteral catheter having an elongate shaft having an outer wall surrounding a lumen, the elongate shaft having a length extending from a proximal end to a distal end and extending in a longitudinal direction, wherein the lumen extends from the proximal end to the distal end, the enteral catheter further comprising a tip at the distal end having a body comprising a collar, an end member, and an opening positioned between the collar and the end member, further wherein the enteral catheter has a size in a range from 5 gauge to 20 gauge; and
    a signal generating apparatus including a signal generator at or near the distal end of the elongated shaft and at least one electrically conductive polymer extending along the entire length of the elongate shaft from the proximal end to the distal end, further comprising a connector comprising at least one electrical contact configured to connect to a wire assembly, wherein the at least one electrically conductive polymer is configured to electrically connect the at least one signal generator to a monitor unit via the wire assembly;
    wherein the outer wall comprises the at least one electrically conductive polymer; and
    wherein the electrically conductive polymer surrounds the at least one signal generator.

2. The tubing assembly of claim 1, wherein the signal generating apparatus is disposed between an inner wall of the elongate shaft and an external surface of the outer wall of the elongate shaft.

3. The tubing assembly of claim 1, wherein the signal generator of the signal generating apparatus is encapsulated by the outer wall of the elongate shaft.

4. The tubing assembly of claim 1, wherein the signal generator is at the distal end of the elongate shaft.

5. The tubing assembly of claim 1, further comprising a plurality of signal generators spaced apart along the elongate shaft.

6. The tubing assembly of claim 1, wherein the at signal generator surrounds the lumen of the elongate shaft.

7. The tubing assembly of claim 6, wherein the signal generator is insulated from the lumen.

8. The tubing assembly of claim 1, wherein the outer wall of the elongate shaft includes an inner layer and an outer layer.

9. The tubing assembly of claim 8, wherein the inner layer and the outer layer coaxially surround the lumen.

10. The tubing assembly of claim 8, wherein the inner layer comprises the at least one electrically conductive polymer of the signal generating apparatus.

11. The tubing assembly of claim 1, wherein the outer wall comprises a single layer, wherein the single layer comprises the at least one electrically conductive polymer of the signal generating apparatus.

12. The tubing assembly of claim 1, wherein an external surface of the outer wall of the elongate shaft is biocompatible.

13. The tubing assembly of claim 1, wherein the signal generating apparatus further comprises a connector assembly configured to transmit at least one electrical signal between the at least one signal generator and the monitor unit.

14. The tubing assembly of claim 1, wherein the electrically conductive polymer is configured to transmit a signal to the signal generator.

15. The tubing assembly of claim 1, wherein the electrically conductive polymer comprises an intrinsically conductive polymer, a conductor-filled polymer or a combination thereof.

16. The tubing assembly of claim 15, wherein the electrically conductive polymer comprises silicone filled with embedded metallic, carbon, graphite or intrinsically conductive polymer particles or powder.

17. The tubing assembly of claim 1, wherein the catheter is a feeding tube.

18. The tubing assembly of claim 1, wherein the connector comprises a conductive metal ring at the proximal end of the elongate shaft in electrical communication with the at least one electrically conductive polymer.

19. A signal generating apparatus comprising:
a signal generator;
at least one electrically conductive polymer; and
a connector comprising at least one electrical contact configured to connect to a wire assembly, wherein the at least one electrically conductive polymer is configured to electrically connect the at least one signal generator to a monitor unit via the wire assembly;
wherein the signal generator and the at least one electrically conductive polymer are configured to be integrated within a catheter comprising a lumen, wherein the at least one electrically conductive polymer is spaced further from the lumen of the catheter in a radial direction than the signal generator, further wherein the at least one electrically conductive polymer is configured to extend continuously from a proximal end of the catheter to a distal end of the catheter and the signal generator is configured to be disposed at or near the distal end of the catheter.

20. The signal generating apparatus of claim 19, further comprising a connector assembly configured to transmit at least one electrical signal between the signal generator and the monitor unit.

\* \* \* \* \*